(12) United States Patent
Baynham

(10) Patent No.: US 9,108,061 B2
(45) Date of Patent: *Aug. 18, 2015

(54) LINEAR ELECTRODE ARRAY TO TREAT MITRAL REGURGITATION

(75) Inventor: Tamara Colette Baynham, Piscataway, NJ (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 828 days.

This patent is subject to a terminal disclaimer.

(21) Appl. No.: 12/843,546

(22) Filed: Jul. 26, 2010

(65) Prior Publication Data

US 2010/0286742 A1    Nov. 11, 2010

Related U.S. Application Data

(63) Continuation of application No. 11/046,214, filed on Jan. 28, 2005, now Pat. No. 7,764,999.

(51) Int. Cl.
  *A61N 1/00* (2006.01)
  *A61N 1/362* (2006.01)

(52) U.S. Cl.
  CPC ..................... *A61N 1/3627* (2013.01)

(58) Field of Classification Search
  CPC .................................................. A61N 1/3627
  USPC ....................................... 607/4–26
  See application file for complete search history.

(56) References Cited

U.S. PATENT DOCUMENTS

| | | | |
|---|---|---|---|
| 4,317,458 A * | 3/1982 | Yokoyama | 607/122 |
| 4,951,682 A * | 8/1990 | Petre | 600/526 |
| 5,554,177 A | 9/1996 | Kieval et al. | |
| 6,643,546 B2 * | 11/2003 | Mathis et al. | 607/9 |
| 6,795,732 B2 | 9/2004 | Stadler et al. | |
| 6,839,592 B2 | 1/2005 | Grandjean | |
| 6,934,586 B2 | 8/2005 | Struble et al. | |
| 7,113,823 B2 | 9/2006 | Yonce et al. | |
| RE39,897 E | 10/2007 | Mower | |
| 7,289,849 B2 | 10/2007 | Baynham | |
| 7,764,999 B2 | 7/2010 | Baynham | |
| 7,953,480 B2 | 5/2011 | Baynham | |
| 2002/0143368 A1 * | 10/2002 | Bakels et al. | 607/9 |
| 2003/0028221 A1 * | 2/2003 | Zhu et al. | 607/9 |
| 2003/0199930 A1 | 10/2003 | Grandjean | |
| 2005/0154422 A1 | 7/2005 | Band et al. | |
| 2005/0261741 A1 | 11/2005 | Libbus et al. | |
| 2006/0173502 A1 | 8/2006 | Baynham | |
| 2006/0173503 A1 | 8/2006 | Baynham | |
| 2006/0173504 A1 | 8/2006 | Zhu et al. | |
| 2006/0173505 A1 | 8/2006 | Salo et al. | |

(Continued)

OTHER PUBLICATIONS

U.S. Appl. No. 11/046,214, Final Office Action mailed Nov. 17, 2008, 6 pgs.

(Continued)

*Primary Examiner* — Scott Getzow

(74) *Attorney, Agent, or Firm* — Schwegman Lundberg & Woessner, P.A.

(57) ABSTRACT

A method and apparatus are disclosed for treating mitral regurgitation with electrical stimulation. By providing pacing stimulation to a region of the left ventricle in proximity to the mitral valve apparatus in a manner which pre-excites the region during early ventricular systole, a beneficial effect is obtained which can prevent or reduce the extent of mitral regurgitation.

17 Claims, 3 Drawing Sheets

(56) References Cited

U.S. PATENT DOCUMENTS

2008/0027497 A1     1/2008    Baynham
2010/0286742 A1    11/2010    Baynham

OTHER PUBLICATIONS

U.S. Appl. No. 11/046,214, Final Office Action mailed Dec. 2, 2009, 6 pgs.

U.S. Appl. No. 11/046,214, Non-Final Office Action mailed May 16, 2008, 6 pgs.

U.S. Appl. No. 11/046,214, Non-Final Office Action mailed Jun. 16, 2009, 7 pgs.

U.S. Appl. No. 11/046,214, Non-Final Office Action mailed Nov. 8, 2007, 6 pgs.

U.S. Appl. No. 11/046,214, Notice of Allowance mailed Mar. 23, 2010, 4 pgs.

U.S. Appl. No. 11/046,214, Response filed Feb. 2, 2010 to Final Office Action mailed Dec. 2, 2009, 6 pgs.

U.S. Appl. No. 11/046,214, Response filed Feb. 7, 2008 to Non-Final Office Action mailed Nov. 8, 2007, 7 pgs.

U.S. Appl. No. 11/046,214, Response filed Apr. 16, 2009 to Final Office Action mailed Nov. 17, 2008, 7 pgs.

U.S. Appl. No. 11/046,214, Response filed Aug. 18, 2008 to Non Final Office Action mailed May 16, 2008, 8 pgs.

U.S. Appl. No. 11/046,214, Response filed Sep. 16, 2009 to Non Final Office Action mailed Jun. 16, 2009, 9 pgs.

U.S. Appl. No. 11/046,215, Advisory Action mailed Mar. 31, 2008, 3 pgs.

U.S. Appl. No. 11/046,215, Final Office Action mailed Jan. 8, 2008, 7 pgs.

U.S. Appl. No. 11/046,215, Non-Final Office Action mailed May 14, 2008, 7 pgs.

U.S. Appl. No. 11/046,215, Non-Final Office Action mailed Jul. 31, 2007, 10 pgs.

U.S. Appl. No. 11/046,215, Response filed Mar. 10, 2008 to Final Office Action mailed Jan. 8, 2008, 5 pgs.

U.S. Appl. No. 11/046,215, Response filed Oct. 31, 2007 to Final Office Action mailed Jul. 31, 2007, 7 pgs.

\* cited by examiner

LINEAR ELECTRODE ARRAY TO TREAT MITRAL REGURGITATION

CLAIM OF PRIORITY

This application is a continuation of and claims the benefit of priority under 35 U.S.C. §120 to U.S. patent application Ser. No. 11/046,214, filed on Jan. 28, 2005, now issued as U.S. Pat. No. 7,764,999, which is hereby incorporated by reference herein in its entirety.

FIELD OF THE INVENTION

This invention pertains to cardiac devices such as pacemakers and other types of devices for treating cardiac dysfunction.

BACKGROUND

The tricuspid and mitral valves, also referred to as the atrioventricular valves, separate the atrium and ventricle on the right and left sides of heart, respectively. The function of the atrioventricular valves is to allow flow of blood between the atrium and ventricle during ventricular diastole and atrial systole but prevent the backflow of blood during ventricular systole. The mitral valve is composed of a fibrous ring called the mitral annulus located between the left atrium and the left ventricle, the anterior and posterior leaflets, the chordae tendineae, and the papillary muscles. The leaflets extend from the mitral annulus and are tethered by the chordae tendineae to the papillary muscles which are attached to the left ventricle. The function of the papillary muscles is to contract during ventricular systole and limit the travel of the valve leaflets back toward the left atrium. If the valve leaflets are allowed to bulge backward into the atrium during ventricular systole, called prolapse, leakage of blood through the valve can result. The structure and operation of the tricuspid valve is similar.

Mitral regurgitation (MR), also referred to as mitral insufficiency or mitral incompetence, is characterized by an abnormal reversal of blood flow from the left ventricle to the left atrium during ventricular systole. This occurs when the leaflets of the mitral valve fail to close properly as the left ventricle contracts, thus allowing retrograde flow of blood back into the left atrium. Tricuspid regurgitation (TR) occurs in a similar manner. MR and TR can be due to a variety of structural causes such as ruptured chordae tendineae, leaflet perforation, or papillary muscle dysfunction. Functional MR and TR may also occur in heart failure patients due to annular dilatation or myocardial dysfunction, both of which may prevent the valve leaflets from coapting properly.

In acute mitral valve regurgitation, the incompetent mitral valve allows part of the ventricular ejection fraction to reflux into the left atrium. Because the atrium and ventricle are not able to immediately dilate, the volume overload of the atrium and ventricle results in elevated left atrial and pulmonary venous pressures and acute pulmonary edema. The reduction in forward stroke volume due to the reflux through the regurgitant valve reduces systemic perfusion, which if extreme enough can lead to cardiogenic shock. In chronic mitral valve regurgitation, on the other hand, the left atrium and ventricle dilate over time in response to the volume overload which acts as a compensatory mechanism for maintaining adequate stroke volume. The left ventricular dilatation, however, may further prevent proper coaptation of the mitral valve leaflets during systolic ejection, leading to progression of the left ventricular dilatation and further volume overload. Patients with compensated MR may thus remain asymptomatic for years despite the presence of severe volume overload, but most people with MR decompensate over the long term and either die or undergo a corrective surgical procedure. In order to provide early and appropriate intervention, patients with MR may be identified by clinical examination and/or with specific imaging modalities such as echocardiography.

SUMMARY

A method and apparatus are disclosed for treating mitral or tricuspid regurgitation with electrical stimulation. In one embodiment, pacing stimulation is provided to a region of the ventricle in proximity to the mitral or tricuspid valve apparatus in a manner which pre-excites the region during early ventricular systole in order prevent or reduce the extent of mitral regurgitation. A more uniform stimulation of the pre-excited region may be obtained by the use of a linear electrode array as disclosed herein.

This summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

The most common method presently available for definitive treatment of MR is surgical intervention involving repair of the mitral valve or replacement with a mechanical or transplanted valve. In order to provide early and appropriate intervention, patients with MR may be identified by clinical examination and/or with specific imaging modalities such as echocardiography. The present disclosure deals with a method and apparatus for treating mitral (or tricuspid) regurgitation with electrical pacing therapy. Pacing therapy applied in this manner may be used to treat MR either in place of or in addition to the conventional surgical options.

Figure 1A:
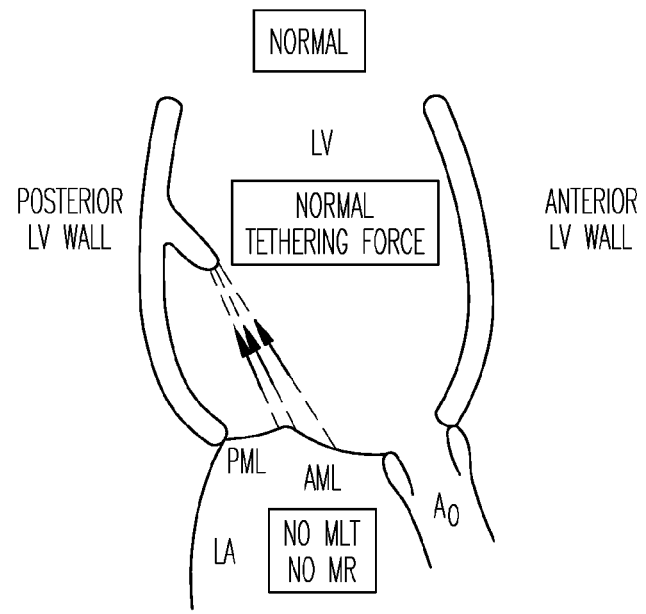
FIGS. 1A and 1B illustrate the mechanisms involved in mitral regurgitation.
Figure 1B:
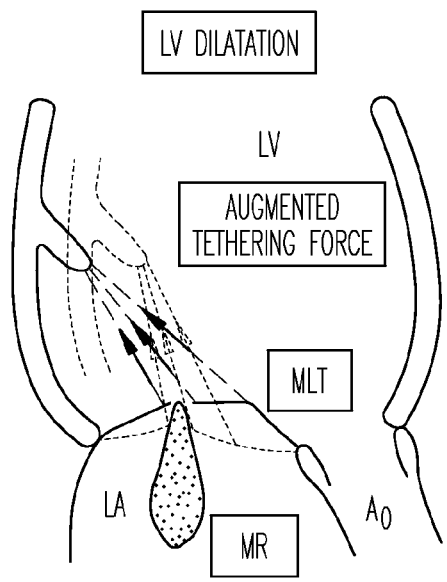

As mentioned above, one mechanism responsible for the development of MR is dilation of the left ventricle which correspondingly dilates the mitral annulus and/or alters its position, thereby preventing proper coaptation of the valve leaflets. Such ventricular dilation occurs in patients suffering heart failure or subsequent to a myocardial infarction as a compensatory response to decreased cardiac output. Heart failure patients may also suffer from electrical conduction deficits which alter the normal activation patterns of the myocardium during systole. Such electrical conduction deficits may result in abnormal timing of papillary muscle contraction which also prevents proper leaflet coaptation. FIGS. 1A and 1B are schematic diagrams of the left ventricle LV, left atrium LA, posterior mitral leaflet PML, anterior mitral leaflet AML, aorta AO, papillary muscle PM, and chordea tendineae CT. FIG. 1A illustrates the normal situation during ventricular systole where the posterior and anterior leaflets are tethered by the chordea tendineae and papillary muscle to the posterior wall of the left ventricle in such a manner that the valve leaflets are coapted, thus preventing reflux flow into the atrium. As the ventricle contracts further, corresponding contraction of the papillary muscle maintains the coaptation of the valve leaflets and prevents them from prolapsing into the atrium. FIG. 1B illustrates the situation where the ventricle is abnormally dilated so as to cause mitral regurgitation. The outward displacement of the ventricular walls and papillary muscle causes an augmented tethering force to be applied to the valve leaflets which prevents proper coaptation and allows reflux flow RF into the atrium. As the ventricle contracts further, simultaneous contraction of the papillary muscle maintains the augmented tethering force and prevents valve closure.

It has been found that pacing therapy may be applied in such a manner that mitral regurgitation is either prevented or lessened in degree in certain patients. In this technique, a pacing electrode is disposed so as to excite a ventricular region in proximity to the regurgitant mitral valve. If the pacing excitation is timed so as to pre-excite the ventricular region in early ventricular systole, the action of the mitral valve is modified in a manner which lessens or prevents regurgitation. This may come about in several different ways. If the ventricular region around the mitral valvular annulus is pre-excited, that ventricular region contracts during the lower afterload pressure which exists during early systole. This may cause the ventricular contraction to constrict the annulus and allow proper coaptation of the valve leaflets to occur. Similarly, pre-excitation of the ventricular region between the valve annulus and the attachment of the papillary muscle to the ventricular wall causes that ventricular region to contract against a lower afterload and lessens the augmented tethering force which prevents proper coaptation of the valve leaflets. Pre-excitation of the papillary muscle can also lessen the augmented tethering force by causing the muscle to be relaxed in later systole and thereby allow valve closure in the dilated ventricle.

As described above, the timing of the pacing delivered to a ventricular region in proximity to the mitral valve should be such that the region is pre-excited during the early phase of ventricular systole. In a patient with intact native atrioventricular conduction, the timing of the pre-excitation may be established with reference to a right or left atrial sense or pace. The atrioventricular delay interval between the atrial sense or pace and the ventricular pre-excitation pace may then be selected to be slightly shorter than the patient's measured intrinsic atrioventricular interval. In one embodiment, because the intrinsic atrioventricular interval varies with heart rate, the intrinsic atrioventricular interval may be measured for a plurality of different heart rate ranges and the atrioventricular delay interval for delivering pre-excitation pacing made to vary accordingly. In a patient either with or without intact native atrioventricular conduction and who is currently receiving conventional bradycardia and/or resynchronization ventricular pacing therapy, the timing of the pre-excitation pacing delivered to a ventricular region in proximity to the mitral valve may be such that the pre-excitation pace occurs before the conventional ventricular pace (or paces), where the latter may be timed with an atrioventricular delay interval selected for optimum hemodynamics. The atrioventricular delay interval for the combination of pre-excitation pacing to the mitral valve region and conventional or resynchronization ventricular pacing may also be made to vary with heart rate.

Described below is an exemplary device which may be used to deliver pre-excitation pacing to the mitral valve region of the left ventricle in any of the manners just described. The device is configurable to also deliver conventional bradycardia or resynchronization pacing in addition to the pre-excitation pacing. It should be appreciated, however, that a device for delivering pre-excitation pacing to the mitral valve region may possess only those features or components necessary for a particular mode of delivery.

1. Exemplary Device Description

Conventional cardiac pacing with implanted pacemakers involves excitatory electrical stimulation of the heart by the delivery of pacing pulses to an electrode in electrical contact with the myocardium. As the term is used herein, a "pacemaker" should be taken to mean any cardiac device, such as an implantable cardioverter/defibrillator, with the capability of delivering pacing stimulation to the heart, including pre-excitation pacing to the mitral valve region as described herein. A pacemaker is usually implanted subcutaneously on the patient's chest, and is connected to electrodes by leads threaded through the vessels of the upper venous system into the heart. An electrode can be incorporated into a sensing channel that generates an electrogram signal representing cardiac electrical activity at the electrode site and/or incorporated into a pacing channel for delivering pacing pulses to the site.

Figure 2:
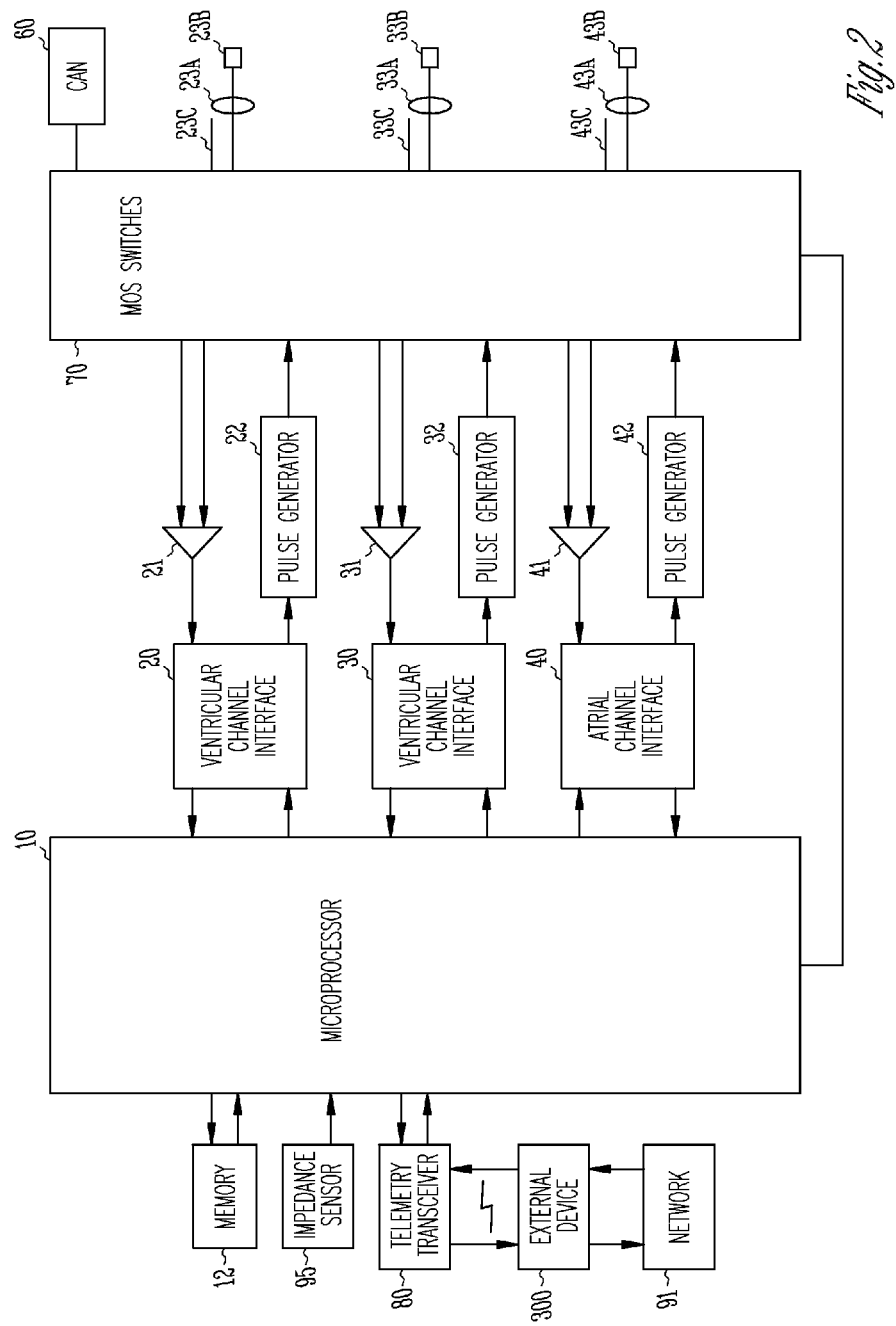
FIG. 2 illustrates an exemplary implantable device for delivering pre-excitation pacing to a mitral valve region.

A block diagram of an implantable multi-site pacemaker having multiple sensing and pacing channels is shown in FIG. 2. The controller of the pacemaker is made up of a microprocessor 10 communicating with a memory 12 via a bidirectional data bus, where the memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. As used herein, the programming of a controller should be taken to refer to either discrete logic circuitry configured to perform particular functions or to the code executed by a microprocessor. The controller is capable of operating the pacemaker in a number of programmed modes where a programmed mode defines how pacing pulses are output in response to sensed events and expiration of time intervals. A telemetry transceiver 80 is provided for communicating with an external device 300 such as an external programmer. An external programmer is a computerized device with an associated display and input means that can interrogate the pacemaker and receive stored data as well as directly adjust the operating parameters of the pacemaker. The telemetry transceiver 80 enables the controller to communicate with an external device 300 via a wireless telemetry link. The external device 300 may be an external programmer which can be used to program the implantable device as well as receive data from it or may be a remote monitoring unit. The external device 300 may also be interfaced to a patient management network 91 enabling the implantable device to transmit data and alarm messages to clinical personnel over the network as well as be programmed remotely. The network connection between the external device 300 and the patient management network 91 may be implemented by, for example, an internet connection, over a phone line, or via a cellular wireless link.

The embodiment shown in FIG. 2 has multiple sensing/pacing channels, where a pacing channel is made up of a pulse generator connected to an electrode while a sensing channel is made up of the sense amplifier connected to an electrode. A MOS switching network 70 controlled by the microprocessor is used to switch the electrodes from the input of a sense amplifier to the output of a pulse generator. The switching network 70 also allows the sensing and pacing channels to be configured by the controller with different combinations of the available electrodes. The channels may be configured as either atrial or ventricular channels allowing the device to deliver conventional ventricular single-site pacing, biventricular pacing, or multi-site pacing of a single chamber, where the ventricular pacing is delivered with or without atrial tracking. In an example configuration, three representative sensing/pacing channels are shown. A right atrial sensing/pacing channel includes ring electrode 43a and tip electrode 43b of bipolar lead 43c, sense amplifier 41, pulse generator 42, and a channel interface 40. A right ventricular sensing/pacing channel includes ring electrode 23a and tip electrode 23b of bipolar lead 23c, sense amplifier 21, pulse generator 22, and a channel interface 20, and a left ventricular sensing/pacing channel includes ring electrode 33a and tip electrode 33b of bipolar lead 33c, sense amplifier 31, pulse generator 32, and a channel interface 30. The channel interfaces communicate bi-directionally with a port of microprocessor 10 and include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. In this embodiment, the device is equipped with bipolar leads that include two electrodes which are used for outputting a pacing pulse and/or sensing intrinsic activity. Other embodiments may employ unipolar leads with single electrodes for sensing and pacing. The switching network 70 may configure a channel for unipolar sensing or pacing by referencing an electrode of a unipolar or bipolar lead with the device housing or can 60.

The controller controls the overall operation of the device in accordance with programmed instructions stored in memory. The controller interprets electrogram signals from the sensing channels, implements timers for specified intervals, and controls the delivery of paces in accordance with a pacing mode. The sensing circuitry of the pacemaker generates atrial and ventricular electrogram signals from the voltages sensed by the electrodes of a particular channel. An electrogram indicates the time course and amplitude of cardiac depolarization and repolarization that occurs during either an intrinsic or paced beat. When an electrogram signal in an atrial or ventricular sensing channel exceeds a specified threshold, the controller detects an atrial or ventricular sense, respectively, which pacing algorithms may employ to trigger or inhibit pacing. An impedance sensor 95 is also interfaced to the controller for measuring transthoracic impedance. The transthoracic impedance measurement may be used to derive either respiratory minute ventilation for rate-adaptive pacing modes or, as described below, cardiac stroke volume for modulating the delivery of pre-excitation pacing to the mitral or tricuspid valve region.

In order to deliver pre-excitation pacing to the mitral valve region of a ventricle, one or more pacing channels are configured, each with an electrode disposed near the region to be pre-excited. Sensing channels for the pre-excited region may or may not also be configured. The pre-excitation ventricular pacing may then be delivered in accordance with a conventional atrial tracking bradycardia pacing algorithm (e.g., VDD or DDD) with the atrioventricular delay interval set to a value which results in pre-excitation of the mitral or tricuspid valve region during ventricular systole. Such pre-excitation pacing of the mitral valve region may also be delivered in conjunction with ventricular resynchronization therapy. Ventricular resynchronization therapy is most commonly applied in the treatment of patients with heart failure due to left ventricular dysfunction which is either caused by or contributed to by left ventricular conduction abnormalities. In such patients, the left ventricle or parts of the left ventricle contract later than normal during systole which thereby impairs pumping efficiency. In order to resynchronize ventricular contractions in such patients, pacing therapy is applied such that the left ventricle or a portion of the left ventricle is pre-excited relative to when it would become depolarized in an intrinsic contraction. Optimal pre-excitation in a given patient may be obtained with biventricular pacing or with left ventricular-only pacing.

In one embodiment, the device is programmed to pace the ventricle with the regurgitant valve at a first programmed AV interval subsequent to an atrial sense or pace and pace the ventricle contralateral to the ventricle with the regurgitant valve at a second programmed AV interval subsequent to an atrial sense or pace. (It should be appreciated that specifying separate AV delay intervals for the two ventricles is equivalent to specifying a biventricular offset interval between right and left ventricular paces.) A patient's intrinsic AV interval between an atrial sense or pace and a sense in the ventricle with the regurgitant valve may be measured, and a programmed AV interval which optimally pre-excites the ventricular region in proximity to the regurgitant valve may be computed as a function of the measured intrinsic AV interval.

2. Electrodes for Pre-Excitation of Mitral Valve Region

Figure 3:
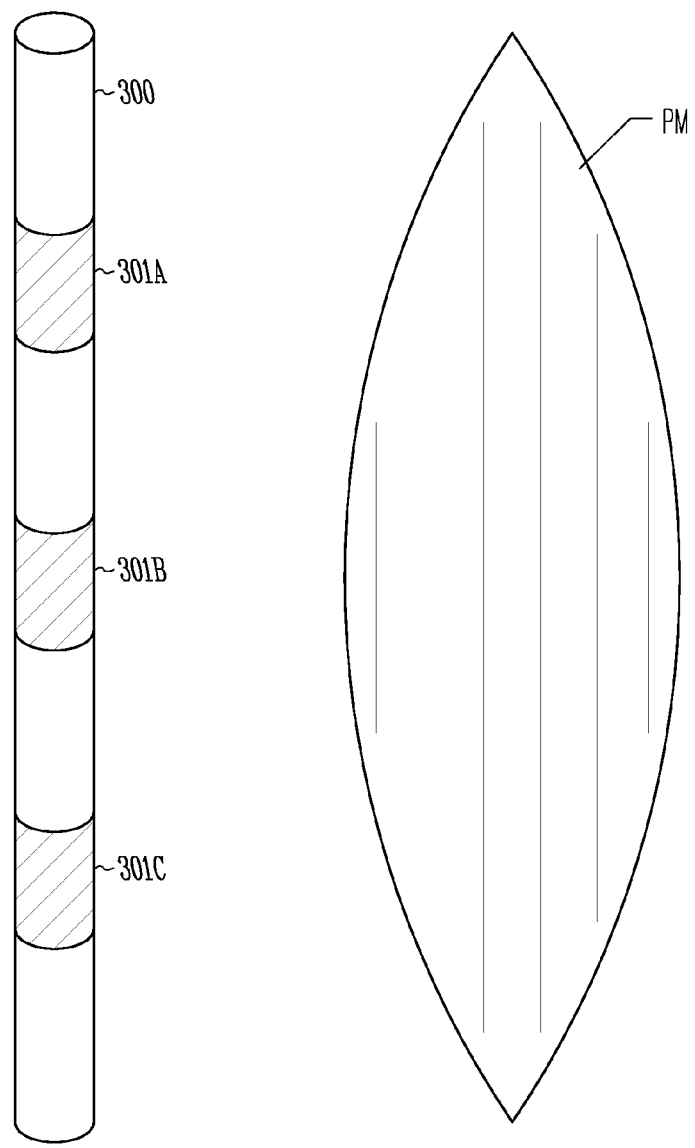
FIG. 3 illustrates an exemplary linear electrode array.

In order to provide optimal pre-excitation pacing to the mitral valve region, the electrical stimulation should be applied in a manner which causes simultaneous depolarization of a selected region of the myocardium. The electric field from a point source such as a conventional pacing electrode uniformly depolarizes only a relatively small myocardial region. In order to provide uniform stimulation to a larger region which encompasses the relevant portions of the mitral apparatus a linear electrode array may be employed as the pre-excitation pacing electrode. Such a linear electrode array may be constructed as an elongated structure with a plurality of electrodes along its length. The plurality of electrodes in the array may be driven by the same or separate pacing channels of the implantable device. A linear electrode array provides more uniform stimulation of a selected myocardial region and facilitates optimal positioning of the electrodes near the region to be pre-excited. The array may be positioned via the coronary sinus or arteries for epicardial activation near the dysfunctional mitral valve region. The linear electrode array may also take the form of a needle-like structure which may be inserted through the myocardium and positioned endocardially adjacent the papillary muscle. FIG. 3 illustrates part of an exemplary linear electrode array 300 having a plurality of electrodes 301a through 301c which is positioned adjacent the papillary muscle PM. Simultaneous activation of the electrodes provides uniform excitation to the papillary muscle which, as described above, can be beneficial in reducing mitral regurgitation.

3. Control of Pre-Excitation Pacing

It may be desirable in certain patients to control the delivery of pre-excitation pacing to the mitral valve region so that such pacing is delivered only when it is needed to lessen mitral regurgitation. Accordingly, the device may be programmed to switch between a first pacing mode which pre-excites the ventricular region in proximity to the regurgitant valve relative to the rest of the ventricle during ventricular systole in order to reduce valve regurgitation and a second pacing mode in accordance with a measured physiological variable. The second pacing mode may be no pacing at all or any other pacing mode such as one which provides ventricular resynchronization therapy. Also, one or more of the programmed AV intervals for the first pacing mode may be made different from the corresponding AV intervals for the second pacing mode, and one or more pacing sites for the first pacing mode may be made different from the pacing sites of the second pacing mode. As mitral regurgitation produces volume overloading of both the left atrium and ventricle, an appropriate physiological variable for the purpose of switching between the first and second pacing modes in order to modulate the frequency or duration of the pre-excitation pacing is cardiac blood volume (or stroke volume). Cardiac blood volume or stroke volume may be determined from a transthoracic impedance measurement using appropriately placed electrodes.

The description set forth above has dealt specifically with techniques and apparatus for treating mitral regurgitation with ventricular pre-excitation pacing. It should be appreciated that same techniques and apparatus could be used to treat either tricuspid or mitral regurgitation by pre-exciting the regurgitant valve region in either ventricle. If both atrio-ventricular valves are regurgitant, pre-excitation pacing may be applied to the atrio-ventricular valve region of both ventricles.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. An implantable cardiac pacing device, comprising:
   pulse generation circuitry for connecting to one or more electrodes and configured to deliver pacing pulses to a cardiac chamber;
   sensing circuitry for connecting to one or more electrodes and configured to detect electrical activity from a cardiac chamber,
   a controller coupled to the pulse generating and sensing circuitry and configured to control the delivery of pacing pulses;
   a switching network operated by the controller for connecting the pulse generation circuitry to one or more selected electrodes;
   wherein, in a first pacing mode, the controller is programmed to connect the pulse generation circuitry to one or more electrodes that are disposed near a ventricular region in proximity to a regurgitant atrio-ventricular valve in the same ventricle as the regurgitant valve and deliver pacing therapy in a manner which pre-excites the ventricular region in proximity to the regurgitant valve relative to the rest of the ventricle during ventricular systole;
   wherein the controller is programmed to measure an intrinsic atrio-ventricular (AV) interval and deliver pacing pulses in the first pacing mode at a first AV delay interval subsequent to an atrial sense or pace, wherein the first AV delay interval is selected to be shorter than the measured intrinsic AV interval;
   wherein, in a second pacing mode, the controller is programmed to connect the pulse generation circuitry to one or more electrodes that are disposed at different locations than the one or more electrodes used in the first pacing mode; and,
   an impedance sensor configurable for sensing transthoracic impedance and measuring cardiac stroke volume; and,
   wherein the controller is programmed to switch to the first pacing mode from the second pacing mode if the stroke volume measurement indicates volume overloading due to the regurgitant atrio-ventricular valve.

2. The device of claim 1 wherein the second pacing mode involves delivering no pacing therapy.

3. The device of claim 1 wherein the second pacing mode provides ventricular resynchronization therapy.

4. The device of claim 1 further comprising a linear electrode array structure having a plurality of electrodes arranged therein for connecting to the pulse generation circuitry and adapted to be disposed near a ventricular region in proximity to a regurgitant atrio-ventricular valve.

5. The device of claim 4 wherein the linear electrode array is a needle-like structure which may be inserted through the myocardium and positioned endocardially adjacent the papillary muscle.

6. The device of claim 1 wherein the controller is programmed to:
   measure an intrinsic AV interval for a plurality of heart rate ranges; and,
   compute the first AV delay interval for delivering pacing pulses in the first pacing mode in accordance with heart rate so as to be shorter than the measured intrinsic AV interval.

7. The device of claim 6 wherein the controller is programmed in the first pacing mode to pace the ventricle contralateral to the ventricle with the regurgitant valve at a second programmed AV interval subsequent to an atrial sense or pace.

8. The device of claim 7 wherein one or more of the programmed AV intervals for the first pacing mode are different from corresponding AV intervals for the second pacing mode.

9. A method for operating a cardiac pacing device, comprising:
   delivering pacing pulses to one or more electrodes disposed near a ventricular region in proximity to a regurgitant atrio-ventricular valve in the same ventricle as the regurgitant valve in a manner which pre-excites the ventricular region in proximity to the regurgitant valve relative to the rest of the ventricle during ventricular systole in a first pacing mode and not delivering such pacing therapy in a second pacing mode;
   measuring an intrinsic atrio-ventricular (AV) interval and delivering pacing pulses in the first pacing mode at a first AV delay interval subsequent to an atrial sense or pace, wherein the first AV delay interval is selected to be shorter than the measured intrinsic AV interval;
   sensing transthoracic impedance and measuring cardiac stroke volume; and,
   switching to the first pacing mode from the second pacing mode if the stroke volume measurement indicates volume overloading due to the regurgitant atrio-ventricular valve.

10. The method of claim 9 wherein the second pacing mode involves delivering no pacing therapy.

11. The method of claim 9 wherein the second pacing mode provides ventricular resynchronization therapy.

12. The device of claim 9 wherein the one or more electrodes is a linear electrode array structure having a plurality of electrodes arranged therein that is disposed near the ventricular region in proximity to a regurgitant atrio-ventricular valve.

13. The method of claim 12 wherein the linear electrode array is a needle-like structure that is inserted through the myocardium and positioned endocardially adjacent the papillary muscle.

14. The method of claim 9 further comprising:
    measuring an intrinsic AV interval for a plurality of heart rate ranges; and,
    computing the first AV delay interval for delivering pacing pulses in the first pacing mode in accordance with heart rate so as to be shorter than the measured intrinsic AV interval.

15. The method of claim 14 wherein the first pacing mode further comprises pacing the ventricle contralateral to the ventricle with the regurgitant valve at a second programmed AV interval subsequent to an atrial sense or pace.

16. The method of claim 15 wherein one or more of the programmed AV intervals for the first pacing mode are different from corresponding AV intervals for the second pacing mode.

17. The method of claim 9 wherein one or more pacing sites for the first pacing mode are different from pacing sites of the second pacing mode.

* * * * *